(12) United States Patent
Taguchi et al.

(10) Patent No.: US 9,428,588 B2
(45) Date of Patent: Aug. 30, 2016

(54) BIO-HYBRID MATERIAL, PRODUCTION METHOD THEREFOR, AND STENT

(75) Inventors: Tetsushi Taguchi, Tsukuba (JP); Makoto Sasaki, Tsukuba (JP); Yasuyuki Katada, Tsukuba (JP)

(73) Assignee: National Institute for Materials Science, Ibaraki (JP)

( * ) Notice: Subject to any disclaimer, the term of this patent is extended or adjusted under 35 U.S.C. 154(b) by 0 days.

(21) Appl. No.: 13/989,279

(22) PCT Filed: Nov. 24, 2011

(86) PCT No.: PCT/JP2011/077021
§ 371 (c)(1),
(2), (4) Date: May 23, 2013

(87) PCT Pub. No.: WO2012/070608
PCT Pub. Date: May 31, 2012

(65) Prior Publication Data
US 2013/0245240 A1    Sep. 19, 2013

(30) Foreign Application Priority Data

Nov. 26, 2010    (JP) ................................ 2010-263403

(51) Int. Cl.
| | |
|---|---|
| C07K 17/14 | (2006.01) |
| A61F 2/82 | (2013.01) |
| A61L 31/02 | (2006.01) |
| A61L 31/16 | (2006.01) |

(52) U.S. Cl.
CPC ................ *C07K 17/14* (2013.01); *A61F 2/82* (2013.01); *A61L 31/022* (2013.01); *A61L 31/16* (2013.01); *A61L 2300/414* (2013.01); *A61L 2300/426* (2013.01)

(58) Field of Classification Search
None
See application file for complete search history.

(56) References Cited

U.S. PATENT DOCUMENTS

| | | | |
|---|---|---|---|
| 7,591,841 B2* | 9/2009 | Hossainy et al. | 623/1.1 |
| 2002/0041933 A1* | 4/2002 | Slone | A01N 25/30 427/384 |
| 2008/0107702 A1 | 5/2008 | Jennissen | |
| 2013/0045277 A1 | 2/2013 | Taguchi et al. | |

FOREIGN PATENT DOCUMENTS

| | | |
|---|---|---|
| EP | 2532373 | 12/2012 |
| JP | 10137334 | 5/1998 |
| JP | A-2004-008634 | 1/2004 |
| JP | A-2006-130007 | 5/2006 |
| JP | 2008007425 | 1/2008 |
| JP | 2009291401 | 12/2009 |
| WO | WO9628475 | 9/1996 |
| WO | WO 2006/056984 | 6/2006 |
| WO | WO 2007/070630 | 6/2007 |
| WO | WO 2011/096402 | 8/2011 |

OTHER PUBLICATIONS

BIODUR datasheet (http://cartech.ides.com/datasheet.aspx?i=101&e=6&c=TechArt; Carpenter products; printed Feb. 26, 2014).*
Koster R, Vieluf D, Kiehn M, et al. Lancet 2000; 356: 1895-7.
Norio Maruyama et al., J. Japan Inst. Metals, vol. 73, No. 1 (2009), pp. 7-14 Fatigue Property of Nickel-Free High Nitrogen Austenitic Stainless Steels in Simulated Body Fluid.
Nobukazu Gyo, Tasuko Abe, Takashi Kitajima, Makoto Sakuragi, Hiroshi Abe, and Yoshihiro Ito, Proceedings of the 39th Medical Polymer Symposium, pp. 73-74 (2010).
International Search Report and Written Opinion for PCT/JP2011/077021.
Japanese Office Action issued in corresponding Japanese Patent Application No. 2012-545781.
Motoki Inoue et al., "UV irradiation enhances the bonding strength between citric acid-crosslinked gelatin and stainless steel", Colloids and Surfaces. B., vol. 88. No. 1, Jun. 29, 2011, pp. 260-264.
EPO Search Report issued in corresponding EPO Patent Application No. 11843764.9.

* cited by examiner

*Primary Examiner* — Brian J Gangle
*Assistant Examiner* — Andrea McCollum
(74) *Attorney, Agent, or Firm* — Hoffmann & Baron, LLP

(57) ABSTRACT

Provided is a bio-hybrid material that does not cause elution of nickel ions and has an excellent endothelialization ability, a production method therefor, and a stent. The bio-hybrid material (101) used includes an alloy part (11) free of Ni, an organic acid (12) having two or more active esters, and a cytokine (13). The alloy part (11) free of Ni forms an ester bond with the organic acid (12), and the organic acid (12) and the cytokine (13) are immobilized via an amide bond.

19 Claims, 9 Drawing Sheets

BIO-HYBRID MATERIAL, PRODUCTION METHOD THEREFOR, AND STENT

TECHNICAL FIELD

The present invention relates to a bio-hybrid material, a production method therefor, and a stent.

Priority is claimed on Japanese Patent Application No. 2010-263403, filed on Nov. 26, 2010, the content of which is incorporated herein by reference.

BACKGROUND ART

In recent years, as treatment for myocardial infarction or angina, coronary interventional procedure using a stent has been mainly performed.

However, since SUS316L or CoCr alloy used for the stent contains nickel ions in general, when the stent is used in the human body, nickel ions are eluted from the materials, and this is pointed out as the cause of restenosis (NPL 1).

Therefore, in order to suppress restenosis accompanied by implantation of a bare-metal stent, a Drug Eluting Stent (DES) containing a drug has been developed. However, the drug eluting stent has a problem that it exhibits a poor endothelialization ability after being implanted.

As a material used for stents, nickel-free high-nitrogen stainless steel (hereinafter, called HNS) has been developed. PTL 2 discloses that HNS can be prepared by electroslag remelting under $N_2$ gas pressure (P-ESR). However, a stent formed of HNS also has a problem that it exhibits a poor endothelialization ability after being implanted.

If cytokine as a molecule that transmits signals to a cell is immobilized onto the surface of a metal, it may be possible to develop a stent having an excellent endothelialization ability without causing the elution of nickel ions. The cytokine includes, for example, Vascular Endothelial Growth Factor (VEGF). PTL 1 relates to effects of immobilized VEGF, and discloses that if VEGF is immobilized onto an artificial blood vessel together with fibronectin, growth of vascular endothelial cells is promoted, and movement speed of the cells increases. Moreover, NPL 3 relates to a cytokine-fixing method, and discloses that cytokine can be immobilized by dopamine treatment performed on the metal surface or a technique using a binding peptide searched by evolutionary molecular engineering.

However, when VEGF is chemically or physically bonded to the surface of a stent formed of HNS by the above-mentioned methods, the binding force becomes too strong, and accordingly, endothelial cells are likely to grow excessively.

CITATION LIST

Patent Literature

[PTL 1] Japanese Unexamined Patent Application, First Publication No. H10-137334

Non-Patent Literature

[NPL 1] Koster R, Vieluf D, Kiehn M, et al., Lancet 2000; 356:1895-7.
[NPL 2] N. Maruyama, M. Sanbe, Y. Katada, K. Kanazawa, J. Japan Inst. Metals 2009; 73:7-14.
[NPL 3] Nobukazu Gyo, Yasuko Abe, Takashi Kitajima, Makoto Sakuragi, Hiroshi Abe, and Yoshihiro Ito, proceedings of the 39th medical polymer symposium, pp. 73-74 (2010)

SUMMARY OF INVENTION

Technical Problem

The present invention aims to provide a bio-hybrid material that does not cause elution of nickel ions and has an excellent endothelialization ability, a production method therefor, and a stent.

Solution to Problem

The present invention has the following configuration.

(1) A bio-hybrid material including: an alloy part free of Ni; an organic acid having two or more active esters; and a cytokine, wherein the alloy part free of Ni forms an ester bond with the organic acid, and the organic acid and the cytokine are immobilized via an amide bond.

(2) The bio-hybrid material according to (1), wherein the cytokine is one selected from a group consisting of VEGF, EGF, FGF, HGF, PDGF, and BMP.

(3) The bio-hybrid material according to (1) or (2), wherein the organic acid having two or more active esters is one selected from a group consisting of citric acid, tartaric acid, malic acid, succinic acid, oxalacetic acid, cis-aconitic acid, 2-ketoglutaric acid, maleic acid, fumaric acid, and any derivative thereof.

(4) The bio-hybrid material according to any one of (1) to (3), wherein the alloy part free of Ni is an alloy containing two or more elements selected from a group consisting of Fe, Mo, Co, and Cr.

(5) The bio-hybrid material according to (4), wherein the alloy contains nitrogen in an amount ranging from 0.5 wt % to 1 wt %.

(6) A production method of a bio-hybrid material including the steps of: surface-treating, in which hydrophilic surface treatment is performed on an alloy part free of Ni; organic acid-immobilizing, in which an organic acid having two or more active esters is immobilized on the alloy part free of Ni; and cytokine-immobilizing, in which a cytokine is immobilized on the organic acid.

(7) The production method of a bio-hybrid material according to (6), wherein the hydrophilic surface treatment is UV irradiation treatment.

(8) The production method of a bio-hybrid material according to (6) or (7), wherein the organic acid is immobilized at a temperature equal to or lower than room temperature.

(9) The production method of a bio-hybrid material according to any one of (6) to (8), wherein the cytokine is immobilized at a temperature equal to or lower than 10° C.

(10) A stent including the bio-hybrid material according to any one of (1) to (5).

Advantageous Effects of Invention

A bio-hybrid material as a first embodiment of the present invention includes an alloy part free of Ni, an organic acid having two or more active esters, and a cytokine, in which the alloy part free of Ni forms an ester bond with the organic acid, and the organic acid and the cytokine are immobilized via an amide bond. Since the bio-hybrid material uses the alloy part free of Ni, elution of nickel ions can be prevented. Moreover, since the cytokine is immobilized in the form of the alloy part free of Ni, the endothelialization ability can be improved. In addition, the alloy layer and the cytokine layer can be more strongly bonded to each other by the organic acid having two or more active esters. For these reasons, a stable bio-hybrid material can be obtained.

A production method of a bio-hybrid material as a second embodiment of the present invention includes a step of surface-treating, in which hydrophilic surface treatment is performed on an alloy part free of Ni, a step of organic acid-immobilizing, in which an organic acid having two or more active esters is immobilized on the alloy part free of Ni, and a step of cytokine-immobilizing, in which a cytokine is immobilized on the organic acid. By the production method of a bio-hybrid material, a bio-hybrid material that does not cause elution of nickel ions and has an excellent endothelialization ability can be easily produced.

A stent as a third embodiment of the present invention is formed of the bio-hybrid material described above. The stent has a high degree of biocompatibility and workability, does not cause elution of nickel ions, and has an excellent endothelialization ability.

DESCRIPTION OF EMBODIMENTS

Embodiments of the Present Invention

[Bio-Hybrid Material]

First, the bio-hybrid material as an embodiment of the present invention will be described.

Figure 1A:
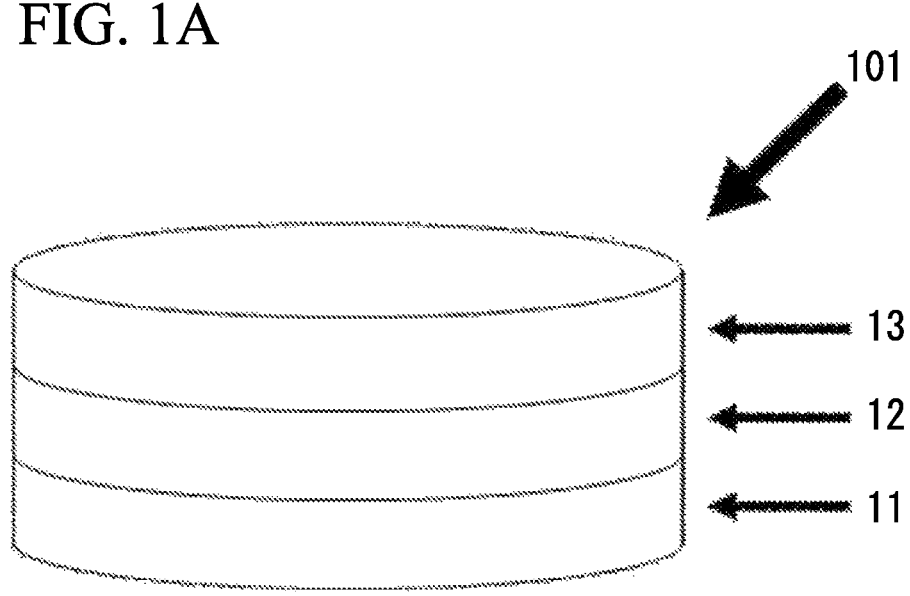
FIG. 1A is a perspective view showing an example of the bio-hybrid material of the present invention.
Figure 1B:
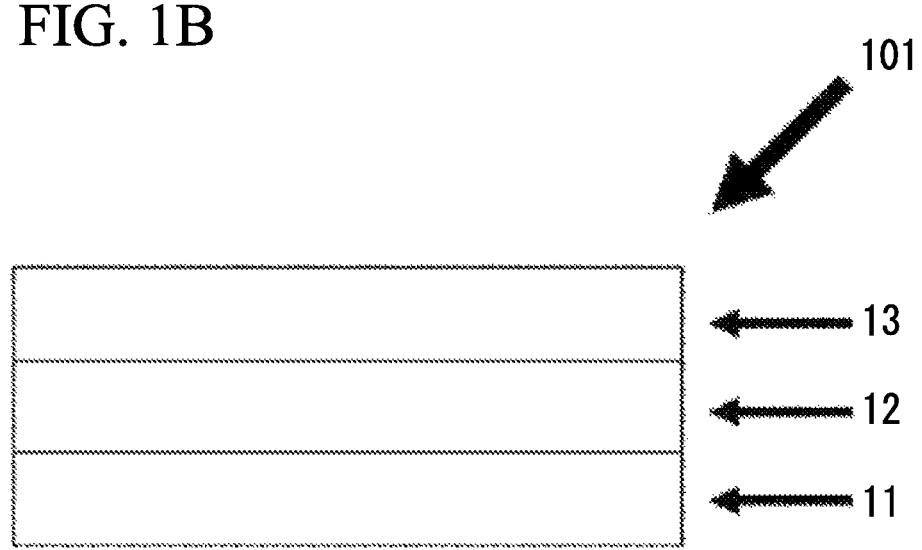
FIG. 1B is a lateral view showing an example of the bio-hybrid material of the present invention.

FIG. 1 is a schematic view showing an example of the bio-hybrid material as an embodiment of the present invention. FIG. 1A is a perspective view, and FIG. 1B is a lateral view.

As schematically shown in FIGS. 1A and 1B, a bio-hybrid material 101 is configured with an alloy part 11 free of Ni, an organic acid 12, and a cytokine 13.

The organic acid 12 is bonded to one surface 11a of the alloy part 11 free of Ni, and the cytokine 13 is bonded to one surface 12a of the organic acid 12.

The cytokine 13 is a molecule that transmits signals to cells and preferably one of Vascular Endothelial Growth Factor (VEGF), Epithelial Growth Factor (EGF), Fibroblast Growth Factor (FGF), Hepatocyte Growth Factor (HGF), Platelet-Derived Growth Factor (PDGF), and Bond Morphogenetic Protein (BMP). If the cytokine 13 is used, it is possible to obtain a bio-hybrid material having an excellent endothelialization ability.

The organic acid 12 has two or more active esters. Having two or more active esters, the organic acid 12 can easily form an amide bond with the cytokine 13 by substituting the active esters. In addition, by using the carboxyl group (—COOH), the organic acid 12 can easily form an ester bond with a hydroxyl group of one surface 11a of the alloy part 11 free of Ni.

The organic acid having two or more active esters is preferably one selected from a group consisting of citric acid, tartaric acid, malic acid, succinic acid, oxalacetic acid, cis-aconitic acid, 2-ketoglutaric acid, maleic acid, fumaric acid, and any derivative thereof Examples of the derivative include tri-succinimidyl citrate (TSC). In the case of TSC, an N-hydroxy succinimide (NHS) group is an active ester group.

In the present specification, the active ester refers to an ester that reacts with an amino group, a hydroxyl group, a thiol group, and the like without addition of a catalyst or the like.

Examples of the active ester include a succinimidyl ester, a sulfosuccinimidyl ester, a p-nitrophenol ester, and the like.

The two or more active esters contained in the organic acid 12 may be the same type of esters or different types of esters.

The alloy part 11 free of Ni is preferably an alloy having two or more elements selected from a group consisting of Fe, Mo, Co, and Cr. In this manner, a stable bio-hybrid material having a high strength can be obtained.

It is preferable that the alloy contain nitrogen in an amount ranging from 0.5 wt % to 1 wt %. If the alloy containing nitrogen in an amount ranging from 0.5 wt % to 1 wt % is used, workability can be improved, and a stent as a fine tube can be easily formed. Accordingly, even a precise stent can be manufactured at a high accuracy. If the amount of nitrogen is less than 0.5 wt %, this is not preferable since biocompatibility deteriorates. If the amount of nitrogen exceeds 1 wt %, this is not preferable since workability deteriorates.

Examples of materials of the alloy part 11 free of Ni that contains nitrogen in an amount ranging from 0.5 wt % to 1 wt % include an alloy of 23Cr-1Mo-1N.

It is more preferable that the alloy contains an element selected from a group consisting of Ti, B, and Nb. If the alloy contains an element selected from a group consisting of Ti B, and Nb, one of TiN, BN, and NbN formed inside the alloy becomes a core of a crystal particle, so the crystal particle can be miniaturized. Accordingly, for example, when this alloy is used for a stent and the like, even if a substrate is caused to have a small thickness, it is possible to enhance the strength of a stent or the like by miniaturizing the crystal particles by means of inhibiting the growth of seed crystals.

Figure 2:
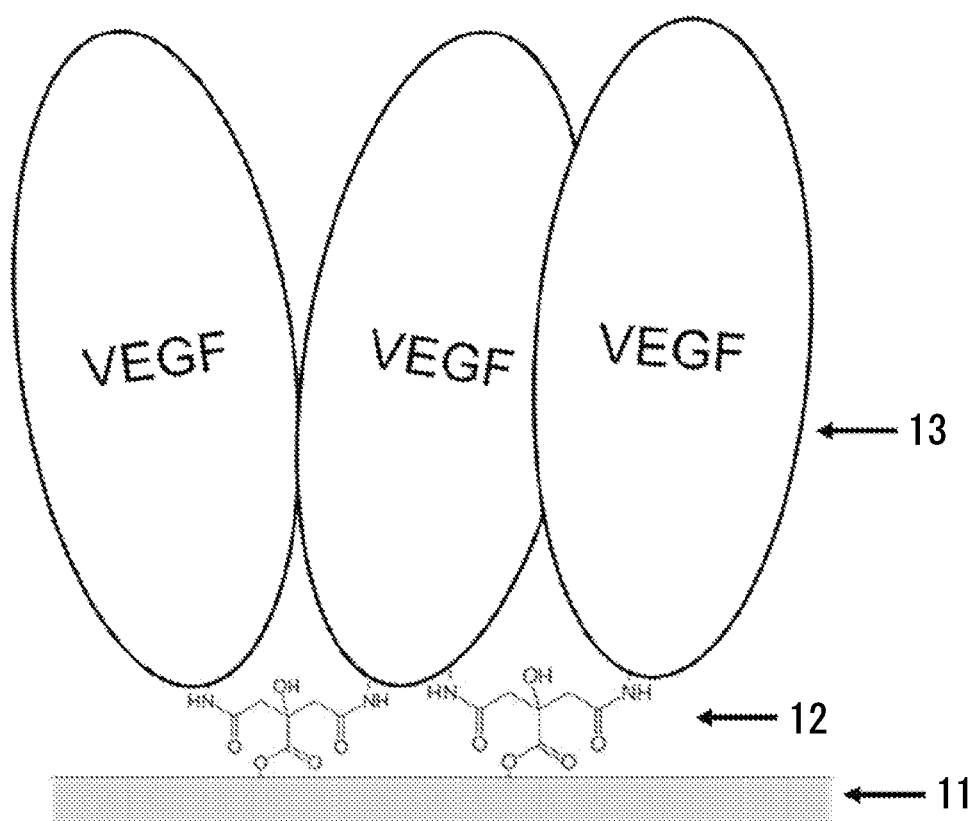
FIG. 2 is an enlarged schematic view showing an example of the bio-hybrid material of the present invention.

FIG. 2 is an enlarged schematic view showing an example of the bio-hybrid material of the present invention. The drawing shows a case where VEGF is used as the cytokine 13, and TSC is used as the organic acid 12.

As shown in FIG. 2, a carboxyl group (—COOH) of TSC forms an ester bond with the alloy part 11 free of Ni. Moreover, two active esters of TSC are reacted with amino groups of VEGF, whereby TSC and VEGF are immobilized on HNS disks by an amide bond. By using TSC as a linker, the respective layers bind strongly to each other.

[Production Method of Bio-Hybrid Material]

Next, the production method of a bio-hybrid material as an embodiment of the present invention will be described.

The production method of a bio-hybrid material as an embodiment of the present invention includes a step (first step) of surface-treating, in which hydrophilic surface treatment is performed on an alloy part free of N, a step (second step) of organic acid-immobilizing, in which an organic acid having two or more active ester groups is immobilized on the alloy part free of Ni, and a step (third step) of cytokine-immobilizing, in which a cytokine is immobilized on the organic acid.

FIG. 3 is a process drawing showing an example of the production method of a bio-hybrid material as an embodiment of the present invention.

(First Step)

Figure 3A:
FIG. 3A is a process drawing showing an example of the production method of a bio-hybrid material of the present invention.

As shown in FIG. 3A, first, the alloy part 11 free of Ni is prepared. For example, an HNS disk (23Cr-1Mo-1N, ϕ10 mm×H 1 mm) can be used. The size of the alloy part 11 free of Ni is not particularly limited.

Thereafter, one surface 11a of the alloy part 11 free of Ni is irradiated with UV. By the UV irradiation, one surface 11a of the alloy part 11 free of Ni can be hydrophilized. When a general UV irradiation device (rated voltage: 8 W, lamp current: 9.5 mA, ultraviolet intensity: 0.085 mW/cm$^2$ (amount of ozone generated: 16 mg/h) is used, if UV irradiation is performed for 30 minutes or longer, it is possible to amplify hydroxyl groups on the alloy surface by removing the organic molecular layer adsorbed onto the surface, and to impart ultrahydrophilicity (contact angle of 10° or less) to the surface of the alloy part 1. The UV irradiation time is more preferably 45 minutes or longer, and even more preferably 60 minutes or longer.

The hydrophilic surface treatment is preferably UV irradiation treatment. In this manner, it is possible to easily and uniformly perform the hydrophilic surface treatment.

(Second Step)

Subsequently, the alloy part 11 free of Ni that has undergone the hydrophilic surface treatment is set in a substrate holder. As the substrate holder, for example, a silicone sheet can be used.

Next, a certain amount of a solution which contains the organic acid 12 at a predetermined concentration is dripped onto the alloy for a predetermined period of time in a dry atmosphere at room temperature. The concentration of the organic acid 12 and the predetermined period of time are not particularly limited. In this manner, the organic acid 12 is immobilized to one hydrophilized surface 11a of the alloy part 11 free of Ni.

Figure 4A:
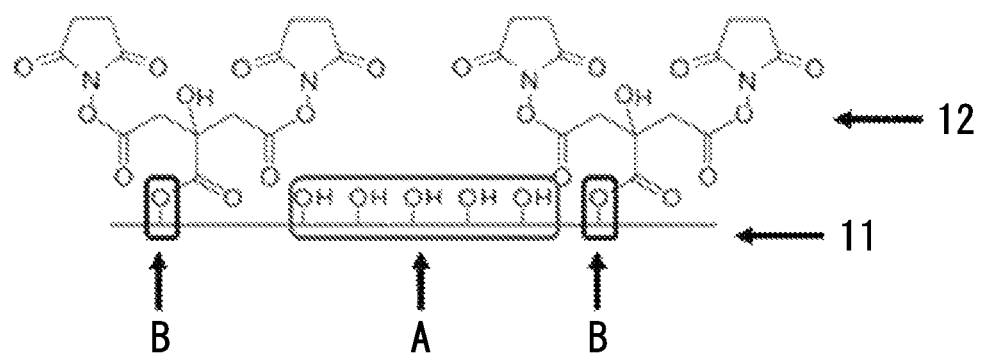
FIG. 4A is an enlarged schematic view showing an example of a state where an organic acid is bonded to a substrate.
Figure 4B:
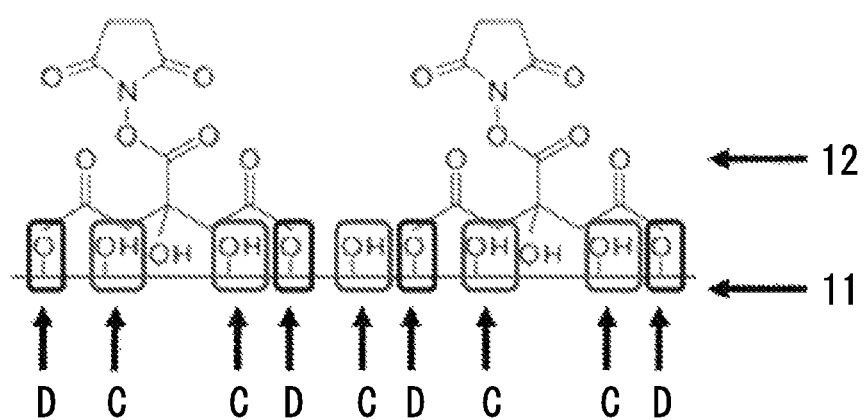
FIG. 4B is an enlarged schematic view showing an example of a state where an organic acid is bonded to a substrate.

FIG. 4 is an enlarged schematic view showing an example of a state where the organic acid is bonded to the substrate. As the organic acid, TSC is used. FIG. 4A is a view showing a case where TSC binds to the alloy part 11 free of Ni via one arm, and FIG. 4B is a view showing a case where TSC binds to the alloy part 11 free of Ni via two arms.

FIG. 4A shows a case where TSC binds to the alloy part 11 free of Ni via one arm, and none of the two active esters are used for the binding of TSC to the alloy part 11 free of Ni. In this case, all of the two active esters can be used for forming an amide bond with cytokine. Moreover, among hydroxyl groups formed on one surface of the alloy part 11 free of Ni, the hydroxyl group of the portion B has been used for the binding of the alloy to the organic acid 12, but the hydroxyl groups of the portion A have not bound to the organic acid 12.

On the other hand, FIG. 4B shows a case where TSC binds to the alloy part 11 free of Ni via two arms, and one of the two active esters is used for the binding of TSC to the alloy part 11 free of Ni. In this case, only one of the active esters can be used to form an amide bond with cytokine. Moreover, among hydroxyl groups formed on one surface of the alloy part 11 free of Ni, the hydroxyl group of the portion D has been used for the binding of the alloy to the organic acid 12, but the hydroxyl group of the portion C has not bound to the organic acid 12.

It is preferable that the organic acid 12 be immobilized at a temperature equal to or lower than room temperature (25° C.). If it is immobilized at a temperature equal to or lower than room temperature, the organic acid 12 can be immobilized without being decomposed. When the organic acid 12 is immobilized under a condition of temperature exceeding room temperature, the organic acid 12 is decomposed in some cases.

Thereafter, an operation, in which the alloy part 11 free of Ni to which the organic acid 12 has been immobilized is subjected to nitrogen blowing and washed with an organic solvent, is repeated. The number of times of nitrogen blowing and washing and the type of the organic solvent are not particularly limited.

Subsequently, after being dipped in an organic solvent for a predetermined period of time at room temperature, the resultant is subjected to nitrogen blowing again and then dried in vacuum for a predetermined period of time at room temperature.

Figure 3B:
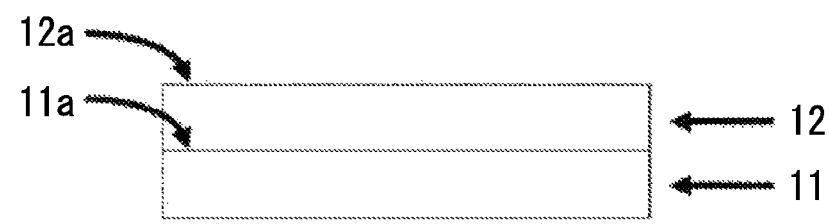
FIG. 3B is a process drawing showing an example of the production method of a bio-hybrid material of the present invention.

By the above-mentioned steps, the organic acid 12 can be immobilized to one surface 11a of the alloy part 11 free of Ni, as shown in FIG. 3B.

In these steps, an organic solvent appropriately selected from DMSO, hexafluoroisopropanol (hereinafter, called HFIP), and the like, can be used. Moreover, as the organic solvent used for washing and dipping after nitrogen blowing, a volatile solvent such as HFIP is preferable.

(Third Step)

Next, the alloy part 11 free of Ni to which the organic acid 12 has been immobilized is set in a substrate holder.

Figure 3C:
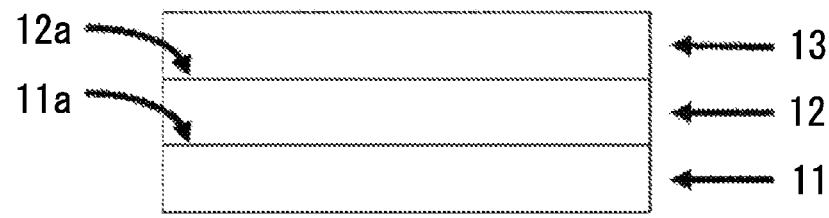
FIG. 3C is a process drawing showing an example of the production method of a bio-hybrid material of the present invention.

Thereafter, a certain amount of a solution containing the cytokine 13 at a predetermined concentration is dripped for a predetermined period of time to one surface 12a of the organic acid 12 on the alloy part 11 free of Ni to which the organic acid 12 has been immobilized. As a solvent for the solution containing cytokine 13, for example, a Phosphate Buffered Saline (PBS) solvent can be used. In this manner, the cytokine 13 is immobilized onto the organic acid 12 on the alloy part 11 free of Ni to which the organic acid 12 has been immobilized, as shown in FIG. 3C.

The cytokine 13 is preferably immobilized at a temperature equal to or lower than 10° C., and more preferably immobilized at a temperature equal to or lower than 4° C. If the cytokine 13 is immobilized at a temperature equal to or lower than 10° C., it is possible to inhibit deactivation of the cytokine. When the cytokine 13 is immobilized under a condition of temperature exceeding 10° C., the cytokine 13 inactivates in some cases.

Subsequently, an operation, in which the alloy part 11 free of Ni to which the cytokine 13 and the organic acid 12 have been immobilized is subjected to nitrogen blowing and washed with distilled water, is repeated. The number of times of nitrogen blowing and washing is not particularly limited.

Thereafter, after being washed with distilled water for a predetermined period of time at room temperature, the resultant is subjected to nitrogen blowing again and then dried in vacuum for a predetermined period of time at room temperature.

By the above step, as shown in FIG. 3C, the cytokine 13 can be immobilized to one surface 12a of the organic acid 12 immobilized to one surface 11a of the alloy part 11 free of Ni.

[Stent]

Next, the stent as an embodiment of the present invention will be described.

Figure 5A:
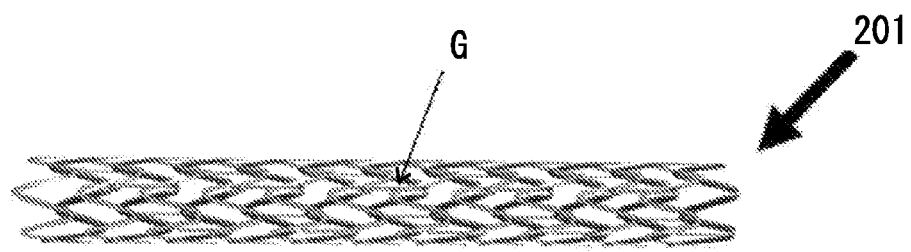
FIG. 5A is a schematic view showing an example of the stent of the present invention.
Figure 5B:
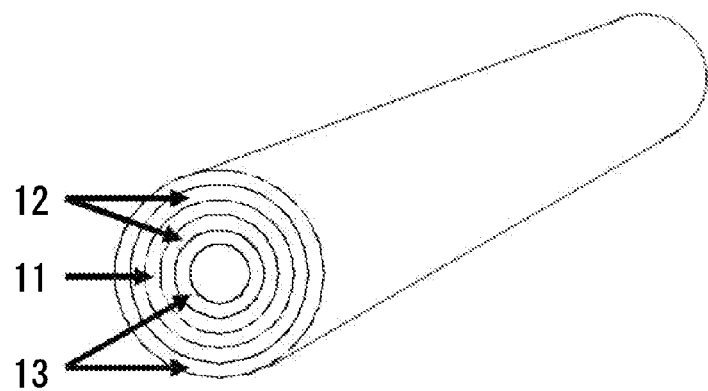
FIG. 5B is a schematic view showing an example of the stent of the present invention.

FIGS. 5A and 5B are schematic views showing an example of the stent as an embodiment of the present invention.

As shown in FIG. 5A, a stent 201 is a network-like tube. As the material constituting the tube, the bio-hybrid material 101 as an embodiment of the present invention is used. Therefore, it is possible to use the stent 201 that does not cause elution of nickel ions and has an excellent endothelialization ability even being used in the human body so as to widen a narrowed or blocked cardiac vessel (coronary artery) and then secure bloodstream.

The size of the tube is not particularly limited. For example, it is possible to use a seamless tube having a diameter of 1.4 mm, a length of 1 cm to 2 cm, and a thickness of 100 μm to 150 μm, and the like.

FIG. 5B is a view showing the portion G of FIG. 5A and is a partial cross-sectional view of the tube configuring the stent 201. The tube constituting the stent 201 is configured with the bio-hybrid material 101 including the cylindrical cytokine 13, the organic acid 12 that is formed to cover the cytokine 13, the alloy part 11 free of Ni that is formed to cover the organic acid 12, the organic acid 12 that is formed to cover the alloy part 11, and the cytokine 13 that is formed to cover the organic acid 12.

The bio-hybrid material 101 as an embodiment of the present invention includes the alloy part 11 free of Ni, the organic acid 12 having two or more active esters, and the cytokine 13. The alloy part 11 free of Ni forms an ester bond with the organic acid 12, and the organic acid 12 and the cytokine 13 are immobilized via an amide bond. Since the bio-hybrid material 101 uses the alloy part 11 free of Ni, elution of nickel ions does not occur. Moreover, since the cytokine 13 is immobilized, the material has an excellent endothelialization ability. In addition, the alloy layer and the cytokine layer can be strongly bonded to each other due to the organic acid 12 having two or more active esters. Accordingly, a stable bio-hybrid material can be obtained.

The bio-hybrid material 101 as an embodiment of the present invention has a configuration in which the cytokine 13 is one selected from a group consisting of VEGF, EGF, FGF, HGF, PDGF, and BMP. Accordingly, the material can be prepared as a bio-hybrid material having an excellent ability to form a cell layer such as vascular endothelium.

The bio-hybrid material 101 as an embodiment of the present invention has a configuration in which the organic acid 12 having two or more active esters is one selected from a group consisting of citric acid, tartaric acid, malic acid, succinic acid, oxalacetic acid, cis-aconitic acid, 2-ketoglutaric acid, maleic acid, fumaric acid, and any derivative thereof. Accordingly, the material can be prepared as a bio-hybrid material in which the cytokine 13 is strongly bonded to the alloy part 11 free of Ni.

The bio-hybrid material as an embodiment of the present invention has a configuration in which the alloy part free of Ni is an alloy that contains two or more elements selected from a group consisting of Fe, Mo, Co, and Cr. Accordingly, the material can be prepared as a stable bio-hybrid material that does not cause elution of nickel ions.

The bio-hybrid material as an embodiment of the present invention has a configuration in which the alloy contains nitrogen in an amount ranging from 0.5 wt % to 1 wt %. Accordingly, the material can be prepared as a stable bio-hybrid material that has a high degree of biocompatibility and workability and does not case elution of nickel ions.

The production method of a bio-hybrid material as an embodiment of the present invention includes a step of surface-treating, in which hydrophilic surface treatment is performed on an alloy part 11 free of Ni, a step of organic acid-immobilizing, in which an organic acid 12 having two or more active ester groups is immobilized on the alloy part 11 free of Ni, and a step of cytokine-immobilizing, in which a cytokine 13 is immobilized on the organic acid 12. Accordingly, by the production method of a bio-hybrid material, it is possible to easily produce the bio-hybrid material 101 that does not cause elution of nickel ions and has an excellent endothelialization ability.

The production method of a bio-hybrid material as an embodiment of the present invention has a configuration in which the hydrophilic surface treatment is UV irradiation treatment. Accordingly, it is possible to easily perform the hydrophilic surface treatment on the alloy part 11 free of Ni, and to easily produce the bio-hybrid material 101.

The production method of a bio-hybrid material as an embodiment of the present invention has a configuration in which the step of organic acid-immobilizing the organic acid is performed under a condition of temperature equal to or lower than room temperature. Accordingly, it is possible to easily produce the bio-hybrid material 101 without decomposing the organic acid 12.

The production method of a bio-hybrid material as an embodiment of the present invention has a configuration in which the step of cytokine-immobilizing is performed under a condition of temperature equal to or lower than 10° C. Accordingly, it is possible to easily produce the bio-hybrid material 101 without decomposing the cytokine 13.

The stent 201 as an embodiment of the present invention is configured so as to be formed of the bio-hybrid material 101. Accordingly, the stent can be prepared as a stent that does not cause elution of nickel ions and has an excellent endothelialization ability.

The bio-hybrid material, production method, and stent as aspects of the present invention are not limited to the above-described embodiments, and can be embodied by being modified in various ways within the scope of technical idea of the present invention. Specific examples of the present embodiment will be shown in the following examples, but the present invention is not limited to these examples.

EXAMPLES

Example 1

A bio-hybrid material of Example 1 was prepared by the following UV irradiation (pretreatment), TSC-fixing treatment, and VEGF-fixing treatment.

[UV Irradiation (Pretreatment)]

First, an HNS disk (23Cr-1Mo-1N, φ10 mm×H 1 mm) was prepared.

Thereafter, UV irradiation was performed on the HNS disk.

Figure 6:
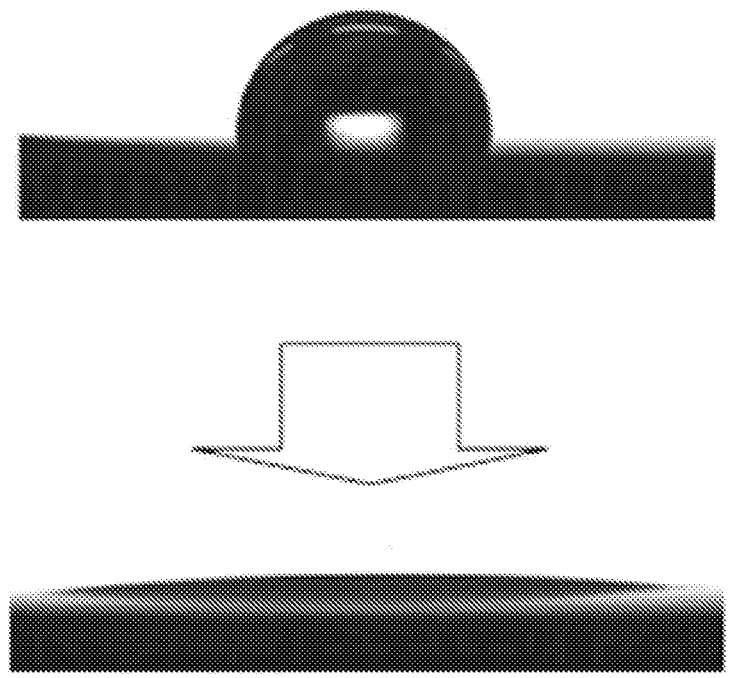
FIG. 6 is a picture showing the difference in a contact angle.

By varying the time of UV irradiation, the contact angle of the surface of HNS disk was measured, and as a result, the results shown in Table 1 were obtained. FIG. 6 is a picture showing the hydrophobic state of the surface of HNS disk before UV irradiation (0 minute) and the hydrophilic state of the surface of HNS disk before UV irradiation (60 minutes). As shown in Table 1 and FIG. 6, the surface became ultrahydrophilic (a contact angle of 10° or less) after 30 minutes, and became further ultrahydrophilic (a contact angle of 5° or less) after 1 hour. From the result, it was considered that the alloy surface was modified to become hydrophibic, and the number of the hydroxyl groups was increased.

TABLE 1

| Time (min) | Contact angle (deg.) |
|---|---|
| 0 | 87 ± 1.32 |
| 15 | 12.3 ± 0.39 |
| 30 | 7.3 ± 1.46 |
| 45 | 4.8 ± 0.14 |
| 60 | 4.4 ± 0.05 |

[TSC-Fixing Treatment]

By the following TSC-fixing protocol, TSC was immobilized onto the surface of the HNS disk having undergone UV irradiation for 60 minutes.

(TSC-Fixing Protocol)

1) After UV irradiation, the HNS disk is set to a silicone sheet.

2) A TSC/DMSO solution of a predetermined concentration is dripped thereto in an amount of 100 μl (in a dry atmosphere for a predetermined period of time at room temperature).

3) After a predetermined period of time, the resultant is subjected to nitrogen blowing and washed once with DMSO.

4) The resultant is subjected to nitrogen blowing, washed twice with HFIP, and then dipped in HFIP (for 1 hour at room temperature).

5) After 1 hour, the resultant is subjected to nitrogen blowing and dried in vacuum (for 12 hours or longer at room temperature).

[VEGF-Fixing Treatment]

By the following protocol, VEGF was immobilized to the surface of the TSC-immobilized HNS.

(VEGF Fixation Protocol)

1) After TSC is immobilized, the HNS disk is set in a silicone sheet.

2) A 1 μg/ml VEGF/PBS solution is dripped thereto in an amount of 100 μl (for 3 hours at 4° C.).

3) After 3 hours, the resultant is subjected to nitrogen blowing and washed three times with distilled water.

4) The resultant is subjected to nitrogen blowing and dried in vacuum (for 12 hours or longer at room temperature).

By the above step, on the HNS disk irradiated with UV for 60 minutes, the TSC-fixing treatment was performed for 60 minutes at a concentration of 20 mM, and then the VEGF-fixing treatment was performed for 3 hours at 4° C. In this manner, the bio-hybrid material of Example 1 was prepared.

For characterization of the immobilized TSC, the contact angle was measured.

For measuring the contact angle, the material of Test example 1 and the materials of Test examples 2 to 6 described below were also prepared for comparison with Example 1.

For the material of Test example 1, the HNS disk was irradiated with UV for 60 minutes, and the TSC-fixing treatment was not performed.

For the materials of Test examples 2 to 6, the TSC concentration at the time of TSC-fixing treatment was set to 20 mM or 100 mM. Moreover, the TSC treatment time at the time of TSC-fixing treatment was set to 5 minutes, 15 minutes, or 60 minutes.

By the above contact angle measurement, the results shown in Table 2 were obtained. As shown in Table 2, as the TSC-fixing treatment proceeded, the contact angle increased, and the property thereof shifted to a hydrophobic property. From the result, it was considered that a more amount of TSC was immobilized.

In addition, by the comparison between Test examples 2 to 6 in Table 2, it became clear that the amount of TSC on the HNS surface was saturated by the treatment that was performed for 15 minutes at a concentration of a dripped solution of 20 mM.

Moreover, the contact angle of the bio-hybrid material of Example 1 became 60° or greater.

TABLE 2

| | Statement of HNS surface | CA (deg.) |
|---|---|---|
| Test example 1 | Hydroxide-HNS | 4.4 ± 0.05 |
| Test example 2 | TSC (20 mM, 5 min)-HNS | 36.0 ± 0.79 |
| Test example 3 | TSC (20 mM, 15 min)-HNS | 42.2 ± 0.94 |
| Test example 4 | TSC (20 mM, 60 min)-HNS | 41.3 ± 0.81 |
| Test example 5 | TSC (100 mM, 15 min)-HNS | 41.6 ± 1.98 |
| Test example 6 | TSC (100 mM, 60 min)-HNS | 43.0 ± 0.97 |
| Example 1 | VEGF-TSC (20 mM, 60 min)-HNS | 61.8 ± 1.95 |

(X-Ray Photoelectron Spectroscopy (XPS) Measurement)

Next, XPS measurement was performed on Test examples 1 and 3 to 6 of Table 2.

FIGS. 7 to 11 show the results of the measured XPS spectrum.

Figure 7:
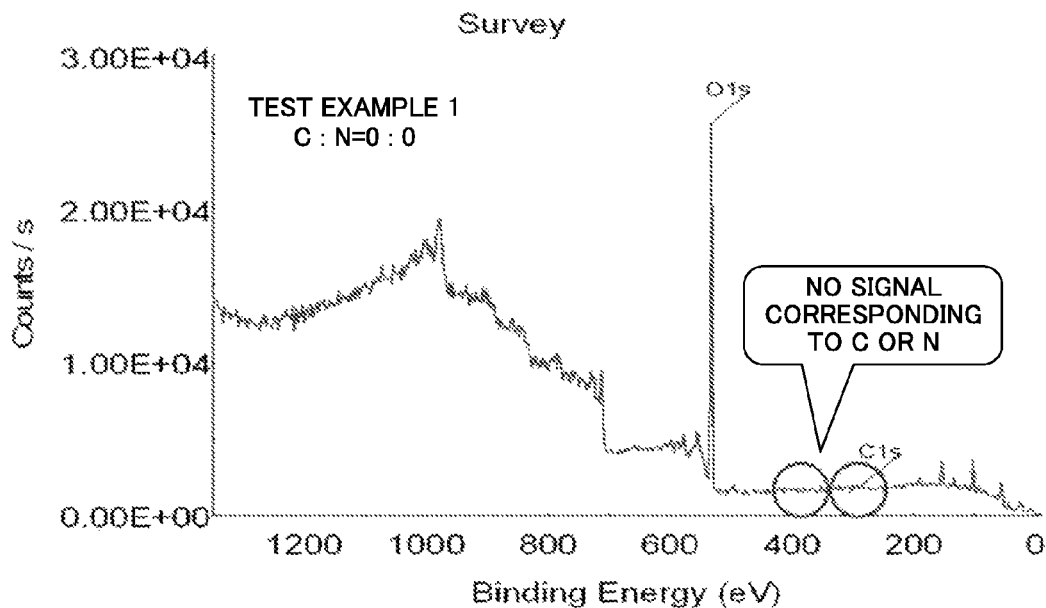
FIG. 7 is an XPS spectrum of Test example 1.
Figure 8:
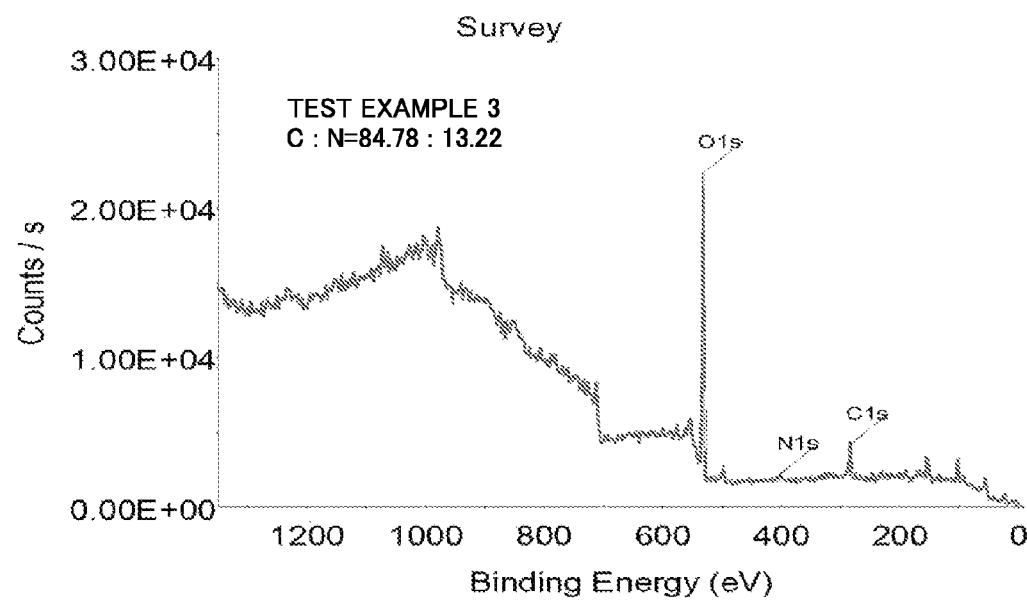
FIG. 8 is an XPS spectrum of Test example 2.
Figure 9:
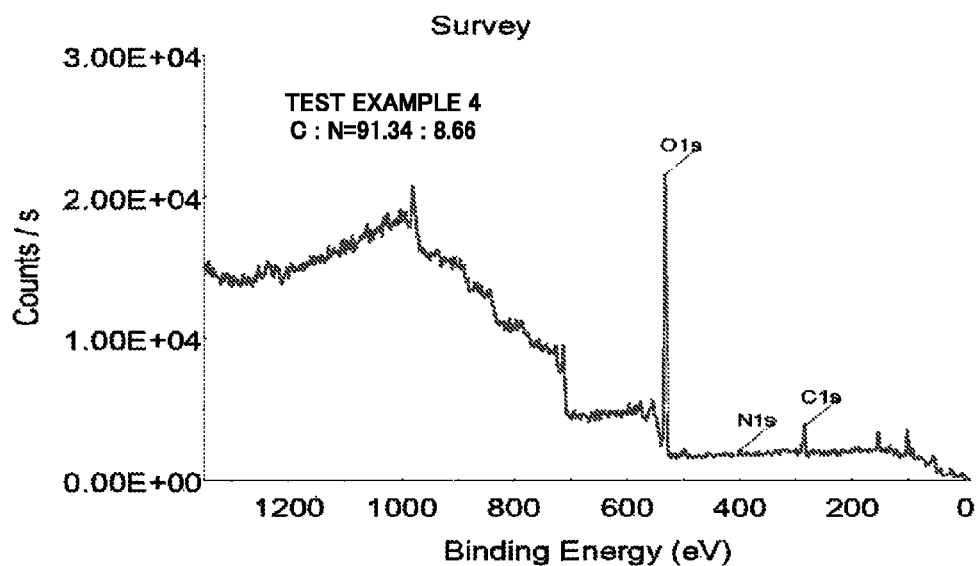
FIG. 9 is an XPS spectrum of Test example 3.
Figure 10:
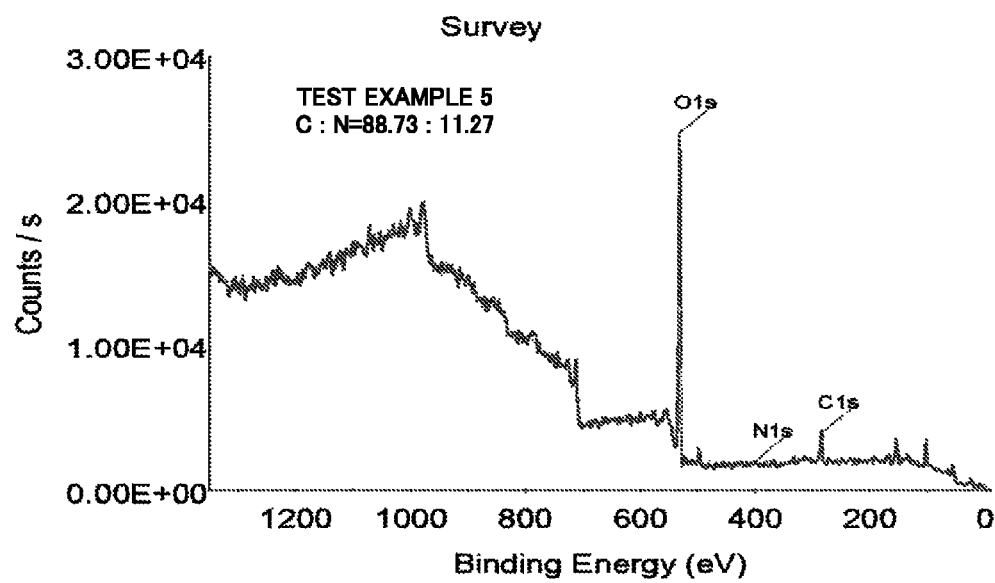
FIG. 10 is an XPS spectrum of Test example 4.
Figure 11:
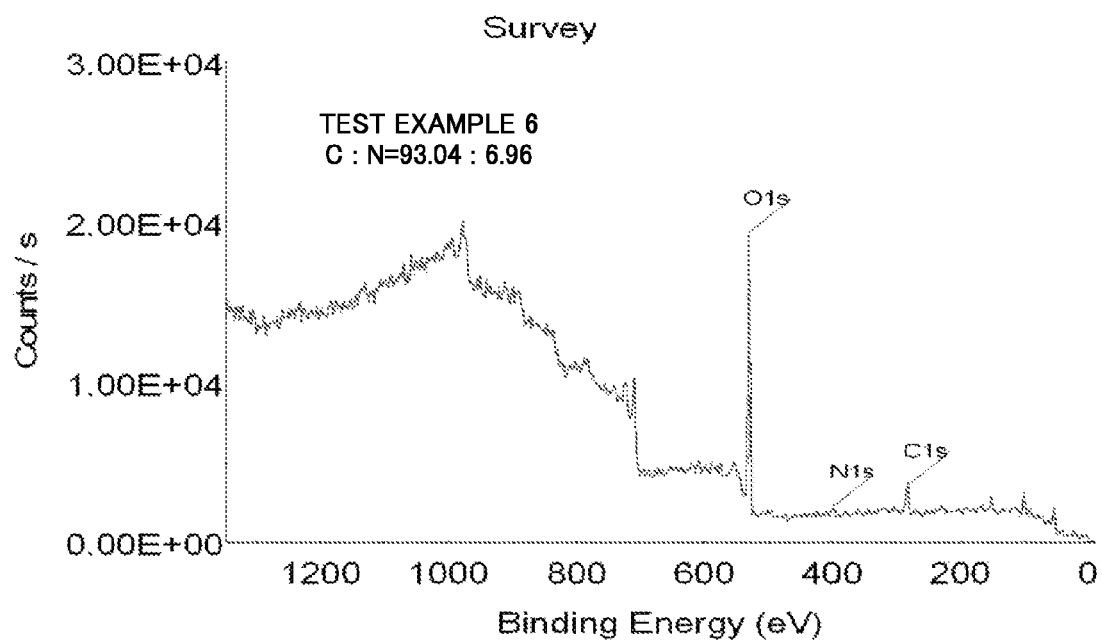
FIG. 11 is an XPS spectrum of Test example 5.

As shown in FIG. 7, signals of C and N were not observed in the disk of Test example 1 having not undergone the TSC-fixing treatment.

On the other hand, as shown in FIGS. 8 to 11, signals of both C and N were observed in the disks of Test examples 3 to 6 having undergone the TSC-fixing treatment.

The ratio of C:N calculated from the signals of C and N varied with the condition of the TSC-fixing treatment.

As one of the reasons, it was considered that this is because an NHS group is dissociated due to the increase in concentration or the elapse of time. N is derived from an active NHS group. Accordingly, it can be mentioned that the higher the proportion of N is, the more the surface is active. This proved that the treatment performed for 15 minutes at a concentration of a dripped solution of 20 mM is optimal.

Moreover, as another reason, it was considered that the variation of the ratio results from the number of arms used for the binding of TSC to hydroxyl groups. As shown in FIG. 4A, when TSC binds to the disk by one arm, the ratio of C:N theoretically becomes 7:1. On the other hand, as shown in FIG. 4B, when TSC binds to the disk by two arms, the ratio of C:N becomes 10:1.

It was considered that the large signal of O observed in the XPS spectra in FIGS. 7 to 11 is derived from hydroxyl groups that remain without binding to the TSC due to the hindrance of the structure of TSC.

Next, a bio-hybrid material of Example 2 was prepared in the same manner as in Example 1, except that the time of TSC-fixing treatment was changed to 15 minutes, and the following characterization was conducted.

Thereafter, ELISA measurement (enzyme immunoassay measurement) was performed on the bio-hybrid material of Example 1 so as to determine the quantity of the immobilized VEGF. As a result, it became clear that the amount of VEGF immobilized is 12.0±1.2 ng/cm².

Subsequently, the bio-hybrid material of Example 1 was examined in terms of retention capacity, by visualization using an enzyme-labeled anti-VEGF antibody that was performed according to the following protocol.

(Protocol)

1) The HNS disk to which VEGF has been immobilized is dipped in a medium (solution used for qualitative evaluation described later) not containing additional factors, at 37° C. for 7 days.

2) After 7 days, the resultant is subjected to nitrogen blowing and washed three times with distilled water.

3) The resultant is dipped in a solution containing a horseradish peroxidase-labeled anti-VEGF antibody (at room temperature for 2 hours).

4) The resultant is washed three times with a buffer and subjected to nitrogen blowing.

5) A solution containing aqueous hydrogen peroxidase and tetramethyl benzidine is dripped onto the HNS disk (at room temperature for 2 hours).

When VEGF has been immobilized to the HNS disk, the horseradish peroxidase-labeled anti-VEGF antibody binds thereto. On the other hand, tetramethylbenzidine stains the disk when horseradish peroxidase coexists with hydrogen peroxidase.

It became clear that the bio-hybrid material of Example 1 is immobilized onto the HNS surface for 7 days or longer without being dissociated, in the medium not containing additional elements.

Next, a bio-hybrid material of Example 2 was prepared in the same manner as in Example 1, except that the time of TSC-fixing treatment was changed to 15 minutes, and the following qualitative evaluation was conducted.

(Qualitative Evaluation)

A disk as a target is set in a 48-well culture plate. 0.5 ml of a basal medium for vascular endothelial cells (EBM-2 medium, manufactured by Cambrex Corporation, not containing additional factors: called EBM-2 hereinafter) is used as a medium, and normal Human Umbilical Vein Endothelial Cells (hereinafter, abbreviated to HUVEC) are seeded to each well at $2.5 \times 10^4$ cells/well. The cell number after 1, 3, and 7 days was counted by a cell number counting device (Premix WST-1 Cell Proliferation Assay System: called WST-1 hereinafter).

As targets, the bio-hybrid material of Example 2 and disks of Comparative examples 1 to 3 shown in Table 3 were used. Moreover, as Test example 7, a case where a disk was not set in a culture plate was also measured.

TABLE 3

|  | Disk | TSC fixation treatment | VEGF fixation treatment |
|---|---|---|---|
| Example 2 | HNS | 20 mM TSC/DMSO (RT, 15 min) | 1 µg/ml VEGF/PBS (4° C., 180 min) |
| Comparative example 1 | HNS | Not performed | Dripping VEGF/PBS at 20 ng/well |
| Comparative example 2 | HNS | Not performed | — |
| Comparative example 3 | SUS 316 | 20 mM TSC/DMSO (RT, 15 min) | 1 µg/ml VEGF/PBS (4° C., 180 min) |
| Test example 7 | None | — | — |

Figure 12:
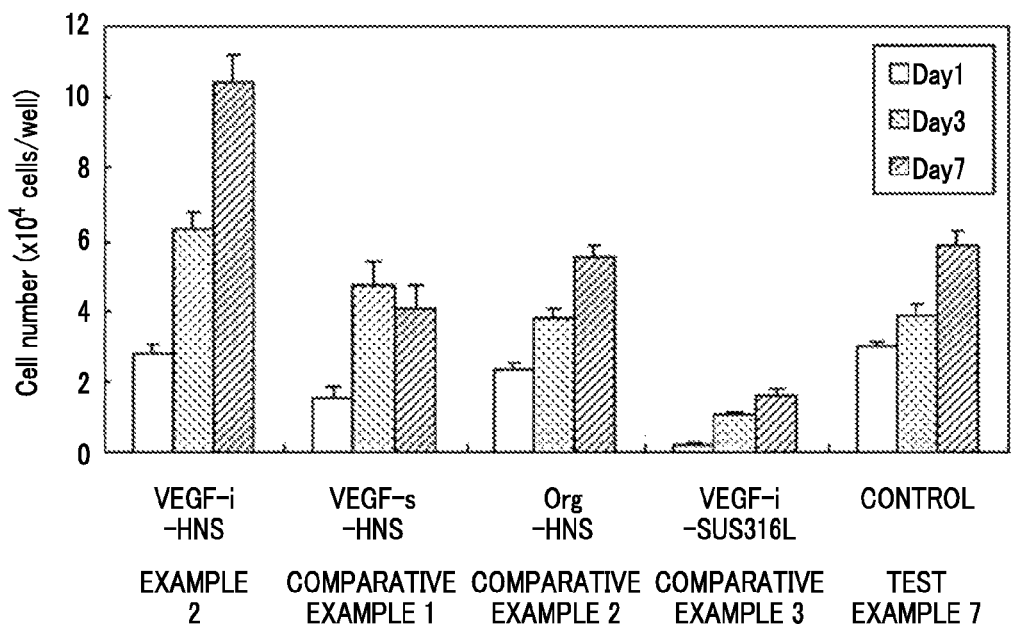
FIG. 12 is a graph showing measurement results.

From the above measurement, the results shown in FIG. 12 were obtained.

It was found that cell number increased further in bio-hybrid material of Example 2 than in Comparative examples 1 to 3 and Test example 7.

INDUSTRIAL APPLICABILITY

The present invention relates to a bio-hybrid material that does not cause elution of nickel ions and has an excellent endothelialization ability, a production method therefor, and a stent. The present invention is applicable to biomaterial and medical instrument industries, and the like.

REFERENCE SIGNS LIST

11: Alloy part free of Ni
11a: One surface
12: Organic acid having two or more active esters
12a: One surface
13: Cytokine
101: Bio-hybrid material
201: Stent

The invention claimed is:

1. A bio-hybrid material comprising:
an alloy part free of Ni;
an organic acid having three or more active ester groups; and
a cytokine,
wherein the alloy part free of Ni forms an ester bond with the organic acid through one of the three or more active ester groups of the organic acid, and the organic acid and the cytokine are immobilized via an amide bond through active ester groups free of the ester bond with the alloy part free of Ni among the three or more active ester groups of the organic acid.

2. The bio-hybrid material according to claim 1, wherein the cytokine is one selected from a group consisting of Vascular Endothelial Growth Factor (VEGF), Epithelial Growth Factor (EGF), Fibroblast Growth Factor (FGF), Hepatocyte Growth Factor (HGF), Platelet-Derived Growth Factor (PDGF), and Bone Morphogenetic Protein (BMP).

3. The bio-hybrid material according to claim 1, wherein the organic acid having three or more active ester groups is one selected from a group consisting of citric acid, oxalacetic acid, cis-aconitic acid, 2-ketoglutaric acid, and any derivative thereof.

4. The bio-hybrid material according to claim 1, wherein the alloy part free of Ni is an alloy containing two or more elements selected from a group consisting of Fe, Mo, Co, and Cr.

5. The bio-hybrid material according to claim 4, wherein the alloy contains nitrogen in an amount ranging from 0.5 wt % to 1 wt %.

6. The bio-hybrid material according to claim 2, wherein the organic acid having three or more active ester groups is one selected from a group consisting of citric acid, oxalacetic acid, cis-aconitic acid, 2-ketoglutaric acid, and any derivative thereof.

7. The bio-hybrid material according to claim 2, wherein the alloy part free of Ni is an alloy containing two or more elements selected from a group consisting of Fe, Mo, Co, and Cr.

8. The bio-hybrid material according to claim 3, wherein the alloy part free of Ni is an alloy containing two or more elements selected from a group consisting of Fe, Mo, Co, and Cr.

9. The bio-hybrid material according to claim 6, wherein the alloy part free of Ni is an alloy containing two or more elements selected from a group consisting of Fe, Mo, Co, and Cr.

10. The bio-hybrid material according to claim 7, wherein the alloy contains nitrogen in an amount ranging from 0.5 wt % to 1 wt %.

11. The bio-hybrid material according to claim 8, wherein the alloy contains nitrogen in an amount ranging from 0.5 wt % to 1 wt %.

12. The bio-hybrid material according to claim 9, wherein the alloy contains nitrogen in an amount ranging from 0.5 wt % to 1 wt %.

13. The bio-hybrid material according to claim 1, wherein the alloy part free of Ni as an alloy containing an element selected from a group consisting of Ti, B, and Nb.

14. The bio-hybrid material according to claim 4, wherein the alloy part free of Ni as an alloy containing an element selected from a group consisting of Ti, B, and Nb.

15. The bio-hybrid material according to claim 5, wherein the alloy part free of Ni as an alloy containing an element selected from a group consisting of Ti, B, and Nb.

16. A stent comprising the bio-hybrid material according to claim 1.

17. A stent comprising the bio-hybrid material according to claim 2.

18. A bio-hybrid material comprising:
an alloy part free of Ni having a hydroxyl group on a surface;
an organic acid having three or more active ester groups; and
a cytokine,
wherein the alloy part free of Ni forms an ester bond with the organic acid through one of the three or more active ester groups of the organic acid, and the organic acid and the cytokine are immobilized via an amide bond through active ester groups free of the ester bond with the ally part free of Ni among the three or more active ester groups of the organic acid.

19. A bio-hybrid material comprising:
an alloy part free of Ni having a hydroxyl group on a surface;
an organic acid having three or more succinimidyl ester groups; and
a cytokine,
wherein the alloy part free of Ni forms an ester bond with the organic acid through one of the three or more active ester groups of the organic acid, and the organic acid and the cytokine are immobilized via an amide bond through active ester groups free of the ester bond with the ally part free of Ni among the three or more active ester groups of the organic acid.

* * * * *